(12) United States Patent
Stankov

(10) Patent No.: US 7,858,656 B2
(45) Date of Patent: Dec. 28, 2010

(54) CONTROLLED RELEASE FORMULATIONS CONTAINING AN ACTIVE INGREDIENT, PREFERABLY MELATONIN AND THE METHOD OF PREPARATION

(75) Inventor: Bojidar M. Stankov, Milan (IT)

(73) Assignee: Ambros Pharma S.R.L., Milan (IT)

( * ) Notice: Subject to any disclaimer, the term of this patent is extended or adjusted under 35 U.S.C. 154(b) by 208 days.

(21) Appl. No.: 11/983,958

(22) Filed: Nov. 13, 2007

(65) Prior Publication Data

US 2008/0187587 A1 Aug. 7, 2008

Related U.S. Application Data

(63) Continuation of application No. 09/854,802, filed on May 14, 2001, now abandoned.

(30) Foreign Application Priority Data

May 17, 2000 (IT) .......................... MI2000A1093

(51) Int. Cl.
- *A61K 31/405* (2006.01)
- *A61K 9/24* (2006.01)
- *A61K 9/36* (2006.01)
- *A61K 47/00* (2006.01)
- *A61P 5/00* (2006.01)

(52) U.S. Cl. .......... 514/415; 424/465; 424/468; 424/474; 424/480; 514/769; 514/770; 514/772; 514/772.3; 514/777; 514/781; 514/784; 514/960; 514/961; 514/964

(58) Field of Classification Search .................. None
See application file for complete search history.

(56) References Cited

U.S. PATENT DOCUMENTS 5,879,710 A * 3/1999 Bromet ........................ 424/487

OTHER PUBLICATIONS

Lee et al., "Controlled release of dual drug-loaded hydroxypropyl methylcellulose matrix tablet using drug-containing polymeric coatings", International Journal of Pharmaceutics (1999), vol. 188, No. 1, pp. 71-80.*
Ex parte Stankov (BPAI, Sep. 20, 2007), pp. 1-11.*
Material Safety Data Sheet-Aerosil 200 (1990), pp. 1-3.*

* cited by examiner

*Primary Examiner*—Johann R Richter
*Assistant Examiner*—Frank I Choi
(74) *Attorney, Agent, or Firm*—Lucas & Mercanti, LLP

(57) ABSTRACT

A controlled release melatonin tablet having a slow release nucleus of melatonin, hydroxypropyl methylcellulose, a lubricant, a volume excipient and a glidant, wherein 95% of the melatonin is released within 5 hours in an oscillating tray containing gastric/intestinal juice at 37° C. and a fast release cortex coating on said nucleus of melatonin, hydroxypropyl methylcellulose and a volume excipient, wherein at least 95% of the melatonin is released within 10 minutes in an oscillating tray containing gastric/intestinal juice at 37° C.

9 Claims, 1 Drawing Sheet

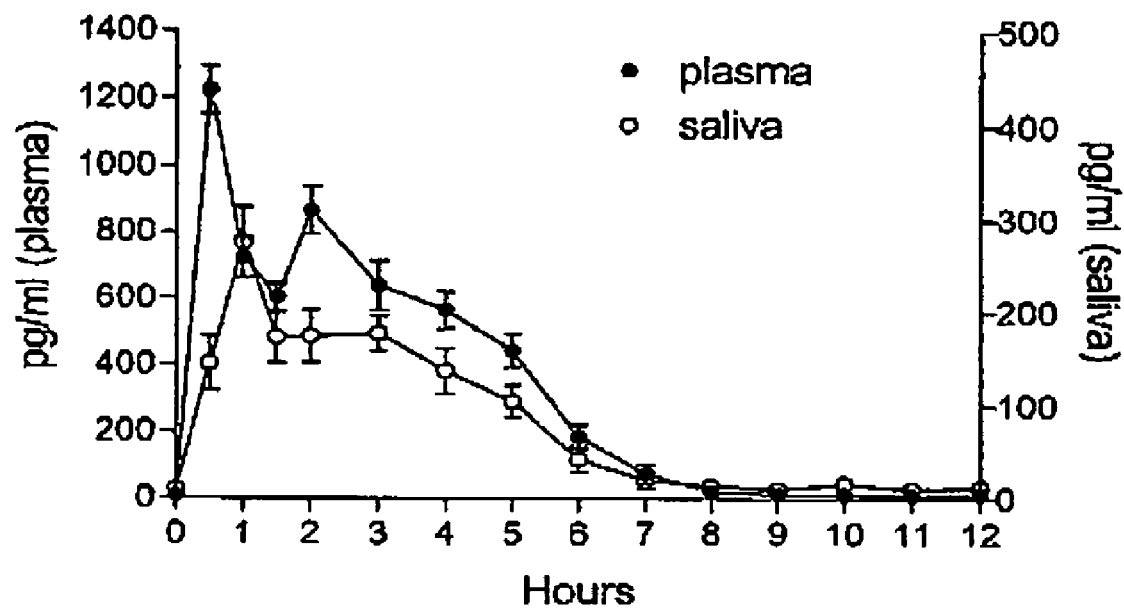

CONTROLLED RELEASE FORMULATIONS CONTAINING AN ACTIVE INGREDIENT, PREFERABLY MELATONIN AND THE METHOD OF PREPARATION

This is a continuation of Ser. No. 09/854,802, filed May 14, 2001 now abandoned.

SUMMARY

This invention relates to new controlled release formulations containing an active ingredient, preferably melatonin, and the method of their preparation. Following their administration, the active ingredient, preferably melatonin, is released in with biphasic pattern and, in particular, rapidly during the first few minutes after its administration and later, slowly and gradually. Formulations obtained by such a process can be usefully employed in cases where controlled release of active ingredients contained in the formulation is needed, for example in disorders in the sleep/wake cycle and sleep disturbances, if they contain melatonin.

FIELD OF APPLICATION

This invention relates to new controlled release formulations containing melatonin, characterized by the fact that the active ingredient is released quickly at first and slowly and gradually later.

Moreover, this invention relates to the use of those controlled release formulations as medicines, nutritional or health food supplements, for the treatment of sleep disturbances and to the new process of preparing controlled release formulations, especially those containing melatonin.

STATE OF THE ART

Melatonin (N-acetyl-5-methoxytryptamine) is an indolic compound widely present in Nature. It is produced by almost all living organisms, from algae to man. While in lower organisms melatonin could be part of the natural defence against oxidative stress, it is widely accepted that in mammals and man melatonin behaves as a Zeitgeber ("time giver"), that acting together with light (primary Zeitgeber), it is capable of synchronizing the endogenous biological clock with the phase of the prevalent photoperiod.

In this way melatonin controls the diurnal (circadian) rhythm of the organism, showing a strong synchronizing effect on the sleep/wake cycle. Because of its marked activity on the circadian clock, melatonin has been used in the treatment of syndromes related to the desynchronization of sleep/wake cycle, as, for example in cases of jet-lag, delayed sleep phase syndrome (DSPS), in blind persons, in the elderly and in insomnia in shift-workers and psycho-physiological insomnia.

Apart of its role in the control of the circadian rhythms, melatonin has also bland hypnotic effects which influence the induction, the depth and the quality of sleep. Indeed, melatonin is capable of improving the sleep micro-structure (CAP and CAP rate) CAP (Cycling Alternating Pattern) is the only objective parameter in establishing sleep quality.

Melatonin is also a strong regulator of body temperature and, since the lowering of body temperature is extremely important for the induction and quality of sleep, this gives further contribution of its effects on sleep.

In normal conditions, the night-time release of melatonin occurs with levels higher than 50-100 pg/ml that, during physiological sleep, last for about 6-7 hours. Under normal conditions melatonin very quickly reaches maximal physiological levels: within 30-45 minutes from the initiation of the nocturnal melatonin peak. This phenomenon has established, in research done on its effects on sleep, the choice of various doses (0.1-1-10-100 mg), a choice determined, on the other hand, by the short half-life of melatonin (20-40 minutes in various species, including man).

Because of the short half-life, the use of low doses melatonin (0.1-1 mg), that correspond to "physiological" levels of melatonin in the peripheral blood, proved to be insufficient for the regulation of the sleep/wake cycle and sleep induction, because following a facilitation of the sleep induction phase, the subject shows the typical tendency to wake up, with high WASO (Wake After Sleep Onset) numerical values both, as the number of awakenings (NA) and as time spent awake after the beginning of the first sleep period.

The administration of high "pharmacological" doses of melatonin is to be as well avoided because of bioavailability of melatonin in the peripheral blood extending in the morning hours, when the melatonin levels physiologically have to be already very low.

In attempts to avoid this, melatonin has been administered in various "retard" formulations (oral, transdermal, transmucosal). However, a great disadvantage of those formulations is the relatively slow absorption of melatonin, often accompanied by low peripheral blood levels, with subsequent loss of the effect on sleep induction. Additionally, the transdermal patches show limited application, because of poor compliance and the danger of leaving (forgetting to take off) the patch in the morning, and therefore having high melatonin levels during daytime (residual release from the patch), when the melatonin levels have to be very low.

On the other hand, the controlled release forms (or pulsatile forms) for oral administration developed recently are very expensive, being prepared as a various number of tablets placed in the same capsule. Moreover, they are not suitable for the preparation of nutritional supplements, because of the use of synthetic retardants and excipients which are not allowed in nutrition and may have untoward effects.

SUMMARY

We have now found, and that is the subject of this invention, new formulations for the controlled release of melatonin able to "mimic" the physiological melatonin pattern in the peripheral blood.

The properties of the new formulations allow to vary the release parameters with the possibility of obtaining a defined biphasic pattern, similar to the natural one observed in the organism during the nocturnal period of synthesis and endogenous release of melatonin.

These new formulations are prepared as a single tablet releasing its melatonin content in a controlled manner with the aim of obtaining a biphasic pattern of release. Both, in vitro and in vivo, there is initially an almost instant release (about 5-10 minutes after administration), of a pre-established percentage (for example between 25% and 30% of the total dose) followed by slow release of the rest of the melatonin contained in the tablet, with the start of the release about 30-45 minutes after administration, with a duration of 5-7 hours.

New slow-release formulations containing melatonin are, therefore, the subject of this invention. They are characterized by the fact they are made up of an internal slow-release, hard "nucleus", with a predetermined content of the active ingredient, and by a quick-release external layer ("cortex"), containing further predetermined doses of melatonin.

The content of melatonin can be between 0.1 and 100 mg inclusive, both in the internal nucleus and in the external "cortex", preferably between 1 and 3 mg in the internal nucleus and between 0.5 and 1.5 mg in the external "cortex".

The formulations according to this invention may be used both as pharmaceuticals and/or nutritional supplements, or functional foods, for the regulation of the sleep/wake cycle, or to substitute the melatonin levels decreasing with age or because of a pathological process.

A further object of this invention is a new process for the preparation of controlled release formulations, in particular those containing melatonin, characterized by the preparation of a nucleus containing an active ingredient, preferably melatonin, with a predetermined rigidity and by overcast of an external layer ("cortex") containing a further predetermined dose of active ingredient, preferably melatonin.

The procedure for the preparation of the said formulations is as follows:
a) preparation of the delayed release nucleus containing the active ingredient, preferably melatonin;
b) forming of the external layer ("cortex") containing a further dose of the main ingredient, preferably melatonin, under control;
c) fixing of the external layer

BRIEF DESCRIPTION OF THE DRAWING

The drawing shows in graphical form the results of Example 3 where the plasma and saliva levels of melatonin were determined for a particular dosage form.

DETAILED DESCRIPTION OF THE INVENTION

The use of formulations containing melatonin for the regulation of the sleep/wake cycle, for sleep induction and to substitute decreased melatonin levels has been known for a long time. In spite of this, up till now the exogenous administration of melatonin still presents serious problems connected with this compound's typical mode of action and its short half-life.

With the aim of obtaining a "physiological" effect it would however be necessary to achieve levels of melatonin able to induce sleep quickly and then to maintain the hormone levels such as to prolong the sleep period. Indeed, this is the only way to physiologically restore the melatonin rhythm and the equilibrium of the disrupted sleep/wake cycle.

As previously mentioned, none of the solutions adopted up until now have resolved this problem satisfactorily.

Moreover, the existing controlled release ("pulsatile-release") formulations, are not suitable for use as nutritional supplements or as foods. This is the preferred use within the embodiment of the present invention, knowing that melatonin shows no significant side-effects and is not a drug, but a natural compound.

With the aim of resolving previously unanswered problems, the Applicant has found new controlled release formulations for the administration of melatonin and a new and advantageous method for the preparation of controlled release formulations.

According to this invention, controlled release formulations are made in the form of a single tablet, characterized by a nucleus which is wrapped in an external layer ("cortex") both containing the active ingredient in predetermined doses.

To verify the effectiveness of the formulations according to the invention, we performed various tests where the doses of melatonin and the excipients used were determined according to the laboratory data and we compared the natural rhythm of melatonin in man, with pharmacokinetics data of the said formulations.

The aim of the invention was to obtain controlled release formulations in which about 100% of the active ingredient contained in the "cortex" is released in a period of between 5-10 minutes from its administration, and 80-90% of the active ingredient contained in the nucleus is released within four hours of its administration.

This biphasic release kinetics corresponds to two peaks in the concentration of melatonin, in the peripheral blood of man which occurs between thirty and one hundred and twenty minutes after its administration, with a bioavailability of about 5-6 hours following administration.

Further object of this invention therefore, is that of making new controlled release formulations available which permit to obtain maximum levels of melatonin in man equivalent to about 1,000-2,000 pg/ml, which correspond to very low pharmacological concentrations, but sufficient to obtain significant effects on the sleep/wake cycle, on sleep induction and structure and to substitute the decreased melatonin levels in cases, when necessary.

The formulations which are the subject of this invention are characterized by an internal nucleus and by an external layer ("cortex") in one single tablet, both containing the active ingredient, preferably melatonin, which releases the active ingredient biphasically.

The melatonin content may be between 0.1 and 100 mg inclusive both in the internal nucleus and in the external "cortex". Preferably, it may be between 1 and 3 mg inclusive in the internal nucleus and between 0.5 and 1.5 mg in the external "cortex".

The excipients used in the preparation of the said formulations can be all those normally used in the field and suitable for the purposes of obtaining the desired controlled release, and in particular, all those permitted for use in the pharmaceutical field and especially in food supplement and/or nutritional field.

The method of preparing controlled release formulations containing the active ingredient, preferably melatonin, according to the invention is as follows:
a) preparation of the delayed release nucleus containing the active ingredient, preferably melatonin;
b) forming of the external layer ("cortex") containing a further dose of the main ingredient, preferably melatonin, under control;
c) fixing of the external cover.

In particular, the new method of preparing controlled release formulations is described as follows:
1) Preparation of the mixture containing the active ingredient, in particular melatonin, for the formulation of a delayed release nucleus with the necessary excipients, in particular volume excipients, gliding and lubricating excipients, binding and retardant excipients.
2) Preparation of the nucleus with a predetermined hardness.
3) Preparation of the active ingredient solution, preferably melatonin, for the formation of the "cortex" of the tablets.
4) Application of the solution under pressure containing the active ingredient to the tablets to make a "cortex", with control of the quantity of the active ingredient by means of chemical analyses done on samples taken during the application. and at the end of the application.
5) For this process all the excipients suitable for the purpose of this invention can be used. In particular for phase 1), dicalcium phosphate, mannitol, lactose, magnesium stearate, polyvinylpyrrolidon, and hydroxypropylmethylcellulose, viscosity 3,000-5,600 can be used, while for phase 3) the preferred choices are hydroxypropylmethylcellulose, lactose, ethyl alcohol and purified water.

EXAMPLE 1

Method for Preparing Tablets Containing Melatonin According to the Invention

Melatonin with a purity defined as HPLC>99.5% from the company HELSINN, (Biasca, Switzerland) was used. The rest of the ingredients were supplied by producers certified for the production and distribution of pharmaceuticals and/or food supplements. Hydroxypropylmethylcellulose (Methocell) with viscosity 3,000-5,600 from Dow Chemical Company was employed.

Preparation of the Tablets

The tablets were produced in five batches: three pilot batches and two experimental batches. The pilot batches were used for the development of the experimental batches.

The preparation was carried out as follows:
1) Preparation of the melatonin mixture for the nucleuss with volume excipients, gliding and lubricating excipients, binding excipients, for example bicalcium phosphate, lactose, aerosil, magnesium stearate, polyvinylpyrrolidon.

A non-limiting example of the granulate formulation is:
1 melatonin 2 mg mannitol 31 mg bicalcium phosphate 30 mg polyvinylpyrrolidon 4.5 mg aerosil 200 (amorphous fumed silicon dioxide) 0.5 mg
2) Granulation
3) Calibration of the granulate
4) Addition of the retardant excipients, lubricants, volume and gliding excipients as, for example, hydroxypropylmethylcellulose, lactose, aerosil, magnesium stearate. A non-limiting example of the unit formulation for the formation of the nucleuss is:

| | |
|---|---|
| granulate (from above) | 68 mg |
| hydroxypropylmethylcellulose | 31 mg |
| lactose | 75 mg |
| aerosil 200 | 0.35 mg |
| Mg stearate | 1.65 mg |

5) Formation of delayed release nucleus: controlled pressure compression in a tablet press to obtain nucleus hardness equal to 7-8 kN
6) Preparation of the melatonin solution for the "cortex" of the tablets, containing the following excipients: hydroxypropylmethylcellulos-e, lactose, ethyl alcohol, purified water. A nonrestrictive example of formulation in solution for the "cortex" is:

| | |
|---|---|
| melatonin | 2.7% |
| hydroxypropylmethylcellulose | 8.8% |
| lactose | 6.4% |
| titanium bioxide | 0.8% |
| ethyl alcohol | 17.3% |
| purified water | 64% |

7) Application of the melatonin solution under pressure on the tablets, for the formation of the "cortex" testing for the quantity of melatonin by means of chemical analyses done on samples taken during manufacture.

Stages 2), 4), and 7) are essential for the preparation of the formulations which are the subject of this invention.

EXAMPLE 2

Test in Vitro for the Release Times of the Active Ingredients

The ready tablets, both in the pilot tests and in the experimental tests, as described above, were subjected to the following physical-chemical tests to obtain the following data:
a) weight uniformity;
b) hardness;
c) friability;
d) average content of melatonin;
e) content uniformity;
f) dissagregation;
g) time for the release of the active ingredient.

Weight uniformity, hardness, friability and disaggregation were checked by means of routine analyses according to standard procedures in the field. The average melatonin content and uniformity of content were determined by determination of the quantity of melatonin in the tablets.

Melatonin Analysis

The pilot batch samples were analysed for their melatonin content by means of direct radioimmunoassay method (RIA), using an anti-melatonin antibody (Stockgrand LTD) and $2-^{125}I$ iodomelatonin (Amersham International) as a tracer. For every test various quantities of crushed tablets or supernatants from tablets incubated in vitro were used. RIA analysis was done in duplicate. Every sample was incubated overnight at 4.degree.C. together with the antibody and tracer.

The separation of the bound melatonin and the free melatonin was carried out by means of incubation with dextran-coated charcoal and subsequent centrifugation (3,000 g at 4.degree. C. for 20 mins.). The supernatant was quickly eliminated and the pellet was counted with a gamma-counter. The lower detection limit of the assay was 10 pg/ml.

The data were later confirmed by HPLC analyses on selected samples, in isocratic system.

Release Times of the Active Ingredient

The tablets prepared for the pilot tests were incubated in gastric/intestinal juices at 37.degree. C. on an oscillating tray and samples from the supernatants were taken out at predetermined times: 1, 5, 10, 30 minutes, 1, 2, 3, 4, 5, and 6 hours. In certain cases the incubation was carried out up to the eighth hour. The samples were analysed for the melatonin content as described above.

The experimental batches were produced on the basis of the data obtained from the pilot batches, and this was followed by the analysis of the content and by establishing the average melatonin contents as previously described for the pilot tests. The determination of the release time was carried out in sixtuplicates for each of the experimental batches (Batch SP-01: 2 mg+1 mg: Batch SP-02: 3 mg+1 mg).

The data in vitro (analyses HPLC) are summarised in Tables I and II.

TABLE I

Release of melatonin from tablets 2 + 1 mg

| Sample | .10 min. Cortex (% of 1 mg) | 1 hour Nucleus (% of 2 mg) | 2 hours Nucleus (% of 2 mg) | 4 hours Nucleus (% of 2 mg) |
|---|---|---|---|---|
| #1 | 104 | 30 | 50 | 77 |
| #2 | 107 | 25 | 48 | 80 |

TABLE I-continued

Release of melatonin from tablets 2 + 1 mg

| Sample | 10 min. Cortex (% of 1 mg) | 1 hour Nucleus (% of 2 mg) | 2 hours Nucleus (% of 2 mg) | 4 hours Nucleus (% of 2 mg) |
|---|---|---|---|---|
| #3 | 105 | 28 | 46 | 79 |
| #4 | 108 | 29 | 47 | 76 |
| #5 | 103 | 26 | 48 | 80 |
| #6 | 109 | 30 | 49 | 76 |
| Average | 106 | 28 | 48 | 78 |

Note:
The data are expressed as percentages of the cumulative release.

TABLE II

Release of melatonin from tablets 3 + 1 mg.

| Samples | 10 min. Cortex (% of 1 mg) | 1 hour Nucleus (% of 3 mg) | 2 hours Nucleus (% of 3 mg) | 4 hours Nucleus (% of 3 mg) |
|---|---|---|---|---|
| #1 | 95 | 24 | 48 | 87 |
| #2 | 98 | 22 | 49 | 83 |
| #3 | 96 | 27 | 47 | 84 |
| #4 | 97 | 25 | 50 | 85 |
| #5 | 99 | 27 | 49 | 86 |
| #6 | 97 | 25 | 47 | 85 |
| Average | 97 | 25 | 48 | 85 |

Note:
The data are expressed as percentages of the cumulative release.

These results in vitro carried out with the experimental batches agreed with the results obtained in the pilot tests and show that the complete release of melatonin from the "cortex" took place within 10 minutes (95-106% of the quantity released); the release of the nucleus at 78-85% took place within four hours, 95% within the fifth hour from the start of incubation.

Laboratory analysis also confirmed weight uniformity; hardness and friability, in the standard set by us; the average melatonin content, homogeneous; the content and disaggregation, uniform.

On the basis of the data obtained, we proceeded to experimentation on healthy volunteers to determine the pharmacokinetics of melatonin.

EXAMPLE 3

Pharmacokinetics in Man (Blood and Saliva: RIA)

Materials and Methods

Subjects

Six adult subjects, 4 males and 2 females with an average age of 35 took part in the test.

The volunteers had previously been informed of the purpose of the research and received a memorandum on how it would take place. All gave verbal consent. All were healthy and had never suffered from any chronic diseases; none of them had taken any medicines for the 2 weeks prior to the test nor during the period of research.

The subjects taking part in the test took one tablet of melatonin (2 mg+1 mg) at 8.45 a.m., in two groups of three subjects. The time of administration was chosen in so as not to interfere with the normal rhythm of melatonin secretion in the 12 hours afterwards. All the volunteers were exposed to light of an intensity of >2000 Lux during the experiment.

In the first stage the determination of melatonin pharmacokinetics after oral administration was carried out by measuring melatonin levels in the plasma and in the saliva of 3 of the subjects for 12 hours following administration (considered as time "0").

Before the administration of melatonin, a sterile heparinized catheter was inserted in the antecubital vein of all the subjects. The obtained heparinized blood samples were immediately centrifuged and the plasma maintained at −20.degree. C. until it was analysed. The saliva samples were taken using special swabs (Salivette, Sarsdet, Germany). At the times indicated above, the volunteers chewed the swabs for about 1 minute. The saliva was later separated by centrifugation at 4° C. and maintained at −20° C. until it was assayed.

The blood and saliva samples were analyzed out simultaneously at times of 0, 30, 60, and 90 minutes and every hour for 12 hours starting from the second hour.

The volunteers were told not to drink coffee or use toothpaste for at least 30 minutes before every saliva sample.

In the second stage of the experiment, melatonin pharmacokinetics was determined in healthy volunteers, carried out by measuring melatonin levels only in the saliva, for 12 hours after administration (0 time). The saliva samples were taken as before at 0, 30, 60 and 90 minutes and every hour for 12 hours starting with the second hour.

Melatonin Content in Plasma and Saliva

All the plasma samples were analysed for their melatonin content by means of direct radioimmunoanalytic method (RIA), using an anti-melatonin antibody (Stockgrand Ltd.) and $2-^{125}I$ iodomelatonin (Amersham International) as tracer.

Two hundred micro-litres of plasma were used for every test. The analysis was carried out in duplicate. Every plasma sample was incubated over-night at 4° C. with the antibody and tracer. The separation of the bound melatonin from the free melatonin was carried out by incubating with dextran-coated charcoal and then centrifuged (3000 g at 4° C. for 20 minutes). The supernatant was rapidly eliminated and the pellet counted with a gamma counter. The lower level of assessment is 10 pg/ml.

Melatonin analysis in saliva was carried out using a direct radioimmunoanalytic method (RIA), using an anti-melatonin antibody (Stockgrand Ltd) and $2-^{125}I$ iodomelatonin (Amersham International) as tracer. Five hundred microlitres were analysed for every saliva sample; the test was duplicated. Every sample was incubated over-night at 4° C. with the antibody and tracer.

The separation of the bound melatonin from the free melatonin was carried out with separation in a liquid phase. A second (anti-IgG antibody) and 6% PEG were added and then incubated for 4 hours at 4° C.

After centrifugation at 3000 g per minute, the supernatant was quickly eliminated and the pellet counted with a gamma-counter. The lower limit of detection was 4 pg/ml. The cumulative results are shown in the drawing.

The following conclusions are drawn from the data obtained:

The melatonin content in the saliva faithfully reflects the pharmacokinetics in the peripheral blood. However, it should be remembered that maximum levels reached in saliva are delayed in comparison with those obtained in blood. This phenomenon is clearly due to the transport of melatonin from the blood to the salivary glands and therefore in the saliva.

The controlled release formula 1 mg+2 mg is suitable for administration in man in that it achieves vary low pharmacological levels (200-1500 pg/ml) for a period of 6-7 hours.

The controlled release formula 1 mg+2 mg results in levels of melatonin in the peripheral blood with a pattern very similar to the natural one (night-time melatonin).

The controlled release formula 1 mg+2 mg is suitable for use in sleep induction because levels of melatonin higher than 1000 pg/ml are obtained in the peripheral blood within 30 minutes from its administration.

The controlled release formula 1 mg+2 mg is suitable for the use in the maintenance of induced sleep because melatonin levels between 250 and 1000 pg/ml are maintained in the peripheral blood for about 6 hours after administration.

Comparable data from the kinetics viewpoint were obtained with the administration of melatonin in the formula 1 mg+3 mg, clearly proving that the invention can be used with different quantities of the active compound.

EXAMPLE 4

Effects on Sleep in Man

Materials and Methods

Subjects and Treatment

Ten patients (average age 56.+−.3.6 years) suffering from psychophysiological insomnia, were used in the study. All of were classified according to The International Classification of Sleep Disorders, Revised Edition, ASDA, 1997. All were informed and gave their verbal consent to take part in the study. All received case report forms to fill in the following parameters: Total Sleep Time (TST), Sleep Latency (SL), Wake After Sleep Onset (WASO), Number of Awakenings (NA).

The treatment was in "crossover" and lasted a week for every formulation. Prior/after (according to a random assignment) to the treatment with controlled release formulations containing melatonin according to this research (1+2 mg of melatonin), the subjects took standard formulations of melatonin in 3 mg tablets, followed by a washout period of three days. In both treatments the tablets were given at 22.30 hours. Then, according to the data gathered, sleep effectiveness was calculated.

Results

The results are summarised in Table III.

TST, SL and WASO are expressed in minutes. NA is the numerical value of the awakenings. SE is the calculated percentage of time spent asleep minus the time spent awake after beginning of sleep.

TABLE III

| Parameter | Baseline | Melatonin Normal | Melatonin Finding |
|---|---|---|---|
| TST | 270 ± .24 | 290. ± 18$^a$ | 330 ± 34$^{a,b}$ |
| SL | 55 ± 5 | 38 ± 5.6$^a$ | 34 ± 83$^{a,b}$ |
| WASO | 42.2 ± 23.1 | 44.2 ± 19.4 | 27.3 ± 10.2$^{a,b}$ |
| NA | 6.2 ± 2.4 | 7.5 ± 2.7 | 4.3 ± 1.6$^{a,b}$ |
| SE (%) | 84.3 | 84.7 | 91.7$^{a,b}$ |

$^a$= significantly different from the Baseline.
$^b$= significantly different from normal Melatonin The above data clearly show that the standard formulations of melatonin, while diminishing sleep latency (SL) and marginally influencing TST, do not have any significant effects on SE, because they do not reduce WASO and NA.

On the contrary, the controlled-release formulations containing melatonin according to this invention, in the same dosage, improved all sleep parameters: TST, SL, WASO, NA and consequently SE.

The data on WASO and NA are to be considered extremely important within the embodiment of this invention for their importance on sleep quality, evidently due to the time-controlled release effect of melatonin.

This invention has the following advantages compared with solutions used until now:
a) only natural compounds are used which are allowed in human nutrition, in opposition to chemical compounds of synthetic origins used in the retard forms or existing time release formulations;
b) the formulation is simple and inexpensive;
c) the formulation consists of a single, small tablet (6 mm. In diameter) and this increases the compliance;
d) the quali-quantitative formulation can be reproduced at industrial level (two batches were produced independently of the pilot batches);
e) the formula is very effective and allows the complete release of the active ingredients in the predicted time.

The formulations according to this invention may also be used for the preparation of functional foods, or herbal products, or nutritional supplements, that is, preparations that within a complex dietary management program may integrate the diet in individuals having intra- and extracellular deficiencies of melatonin and therefore with altered metabolic processes.

According to this invention the formulations can also contain vitamins, minerals, aminoacids, fatty acids, antioxidants, vegetable extracts, animal extracts, or other nutrients or foods as active ingredients, which, within a complex dietary management program may integrate the diet in individuals having intra- and extracellular deficiencies of melatonin and therefore with altered metabolic processes.

The invention claimed is:

1. A controlled release melatonin tablet which consists of:
(a) a slow release nucleus consisting of a granulate containing melatonin, bicalcium phosphate, polyvinylpirrolidone, amorphous fumed silica, hydroxypropylmethylcellulose, lactose and Mg stearate, wherein 95% of the melatonin is released within 5 hours in an oscillating tray containing gastric/intestinal juice at 37° C.; and
(b) a fast release cortex coating on said nucleus which consists of melatonin, hydroxypropylmethylcellulose, lactose and titanium dioxide, wherein at least 95% of the melatonin is released within 10 minutes in an oscillating tray containing gastric/intestinal juice at 37° C.

2. The melatonin tablet as defined in claim 1, wherein the content of melatonin is between 0.1 mg and 100 mg in the slow release nucleus and between 0.1 mg and 100 mg in the fast release cortex.

3. The melatonin tablet as defined in claim 2, wherein the content of melatonin is between 1-3 mg in the slow release nucleus and between 0.5-1.5 mg in the fast release cortex.

4. A method of inducing and maintaining sleep comprising administering the formulation of claim 1 to a subject suffering from a sleep disorder.

5. The method of claim 4, wherein the content of melatonin is between 0.1mg and 100 mg in the slow release nucleus and between 0.1 mg and 100 mg in the fast release cortex.

6. The method of claim 5, wherein the content of melatonin is between 1-3mg in the slow release nucleus and between 0.5-1.5 mg in the fast release cortex.

7. A controlled release melatonin tablet which consists of:
(a) a slow release nucleus consisting of a granulate containing melatonin, bicalcium phosphate, polyvinylpirrolidone, amorphous fumed silica, hydroxypropylmethylcellulose, lactose and Mg stearate which releases the melatonin over a 5 to 7 hour period in vivo; and
(b) a fast release cortex coating on said nucleus consisting of melatonin, hydroxypropylmethylcellulose, lactose and titanium dioxide which releases the melatonin in 5-10 minutes in vivo.

8. The melatonin tablet as defined in claim 7, wherein the content of melatonin is between 0.1 mg and 100 mg in the slow release nucleus and between 0.1 mg and 100 mg in the fast release cortex.

9. The melatonin tablet as defined in claim 8, wherein the content of melatonin is between 1-3 mg in the slow release nucleus and between 0.5-1.5 mg in the fast release cortex.

* * * * *